Figure 1:
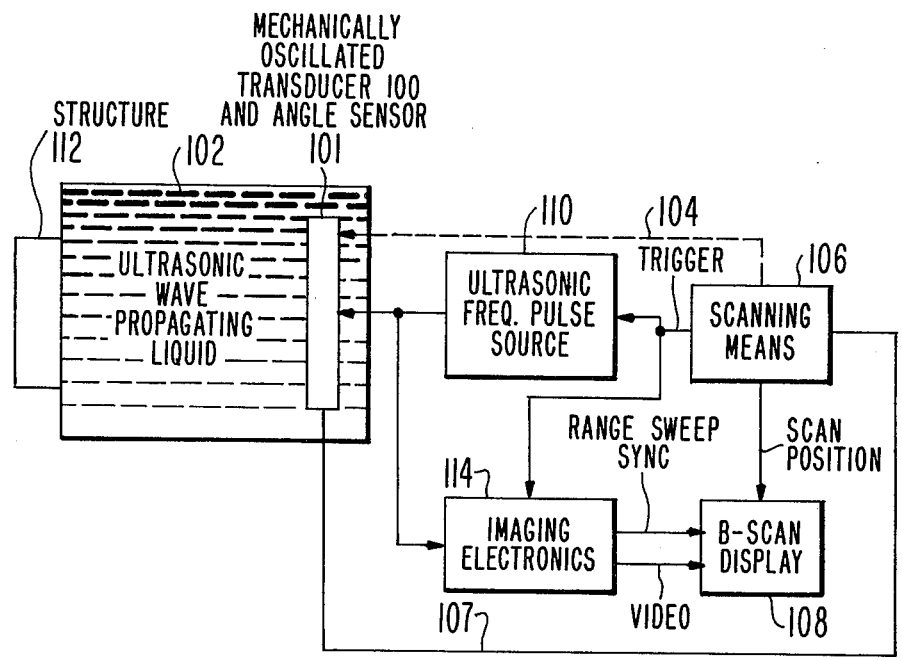

United States Patent [19]

Vilkomerson et al.

[11] 4,277,979

[45] Jul. 14, 1981

[54] SCAN-CONTROL APPARATUS FOR PULSE-ECHO ULTRASONIC IMAGING SYSTEM INCORPORATING OSCILLATED TRANSDUCER

[75] Inventors: David H. R. Vilkomerson, Princeton, N.J.; Reuben S. Mezrich, Miami, Fla.

[73] Assignee: RCA Corporation, New York, N.Y.

[21] Appl. No.: 96,825

[22] Filed: Nov. 23, 1979

[51] Int. Cl.[3] .......................................... G01N 29/04
[52] U.S. Cl. .................................................. 73/633
[58] Field of Search ................ 73/633, 620, 621, 618; 128/660; 367/104

[56] References Cited

U.S. PATENT DOCUMENTS

| Re. 27,650 | 5/1973 | Baum | 367/104 |
|---|---|---|---|
| 3,159,023 | 12/1964 | Steinbrecher | 73/633 |
| 3,248,726 | 4/1966 | Sonnenfeldt | 340/347 P |
| 3,436,720 | 4/1969 | Patterson | 367/104 |
| 3,741,004 | 6/1973 | Posakony | 73/620 |
| 3,752,255 | 8/1973 | Hill et al. | 73/633 |

FOREIGN PATENT DOCUMENTS 1085624  2/1955  France ........................ 73/633

*Primary Examiner*—Anthony V. Ciarlante
*Attorney, Agent, or Firm*—Samuel Cohen; George J. Seligsohn

[57] ABSTRACT

Electronic means, including an analog-to-digital converter responsive to samples of the output from an analog angle sensor directly coupled to an immersed oscillated transducer, is used to trigger the energization of the transducer at each of a predetermined number of equal increments in angle position during each cycle of oscillation of the transducer, with the triggered angle positions during a certain half-cycle of oscillation being interlaced with the triggered angle position during the other half-cycle of oscillation.

5 Claims, 4 Drawing Figures

SCAN-CONTROL APPARATUS FOR PULSE-ECHO ULTRASONIC IMAGING SYSTEM INCORPORATING OSCILLATED TRANSDUCER

This invention relates to scan-control apparatus for a pulse-echo ultrasonic imaging system incorporating an oscillated transducer and, more particularly, to such a system in which the oscillated transducer is immersed in a liquid propagating medium.

Reference is made to our co-pending U.S. Patent Application Ser. No. 964,898, filed Dec. 5, 1978 now U.S. Pat. No. 4,197,751 and assigned to the same assignee as the present application. Our co-pending application discloses a pulse-echo ultrasonic wave energy imaging system, incorporationg a high-angular-velocity oscillated electro-acoustic transducer, for displaying an image of structure, insonified by a scanning beam of pulsed ultrasonic wave energy from the transducer, on a B-scan (or, alternatively, a C-scan) display. The transducer, which is completely immersed in an ultrasonic wave propagating liquid, is mechanically linked to the mechanical portion of scanning means to effect the mechanical oscillation of the transducer. This mechanical portion of the scanning means includes a revolving member, revolved at a uniform angular velocity, for oscillating the transducer through one complete cycle during each revolution of the revolving member. Associated with the revolving member is a digital output angle sensor for dividing each revolution of the revolving member into a predetermined plural number of equal angular samples. The output of this angle sensor is employed by an electronic portion of the scanning means to derive a trigger for an ultrasonic frequency pulse source energizing the transducer and also to derive a scan position signal for the B-scan (or, alternatively, the C-scan) display.

While the pulse-echo ultrasonic wave energy imaging system of the present invention is generally similar to that disclosed in our co-pending U.S. Patent application, the system of the present invention differs therefrom in two significant respects. First, the present invention employs an analog angle sensor which is immersed in the ultrasonic wave propagating liquid and is directly coupled to the oscillating transducer. First, this has the benefit of providing a more accurate measurement of the angular position then occupied by the oscillating transducer than is the case when the angle sensor is only indirectly coupled to the transducer by being associated with the revolving member of the scanning means. Second, the electronic portion of the scanning means employed in the present invention for deriving the trigger and scan position signal differs substantially from that disclosed in our co-pending application.

Figure 1A:
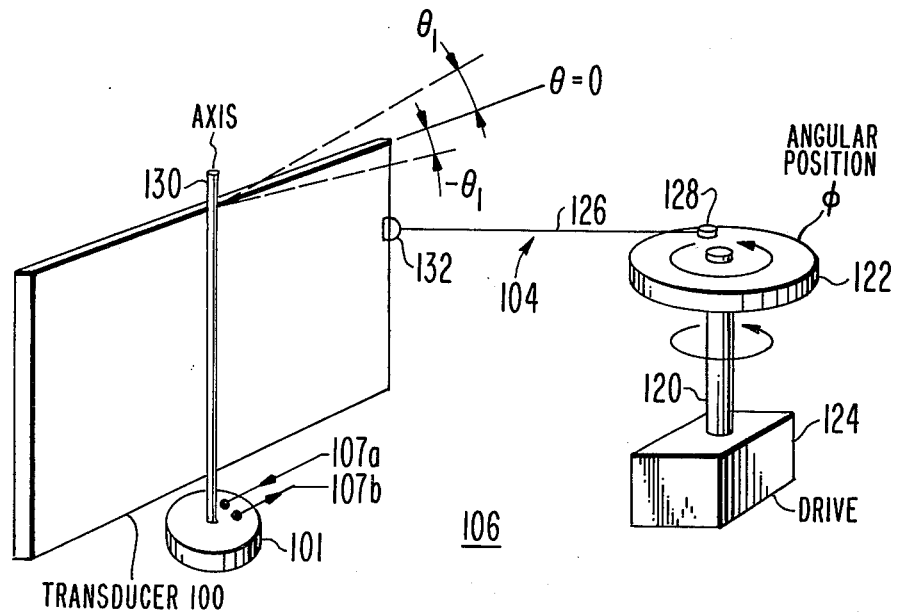
Figure 2:
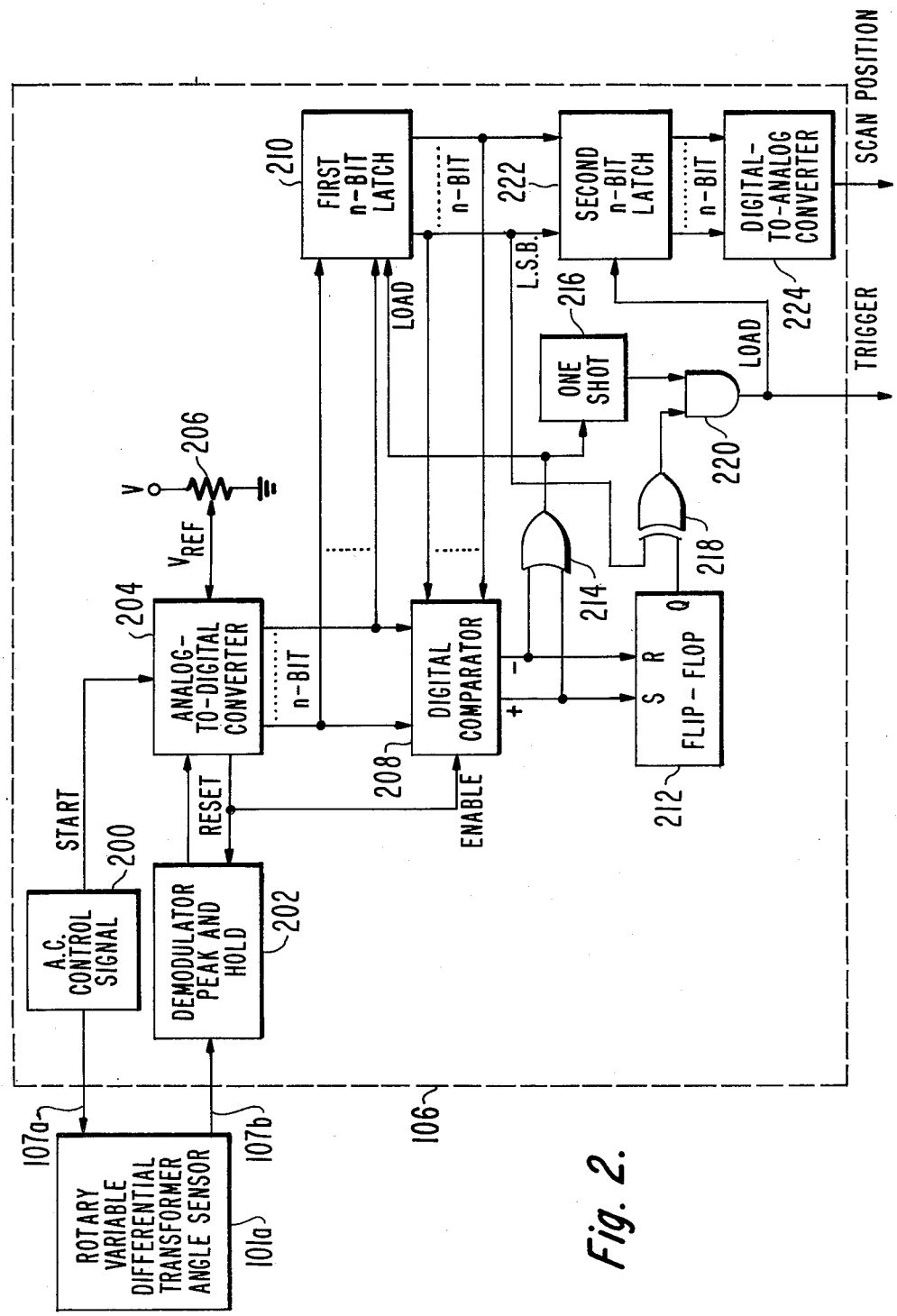
Figure 3:
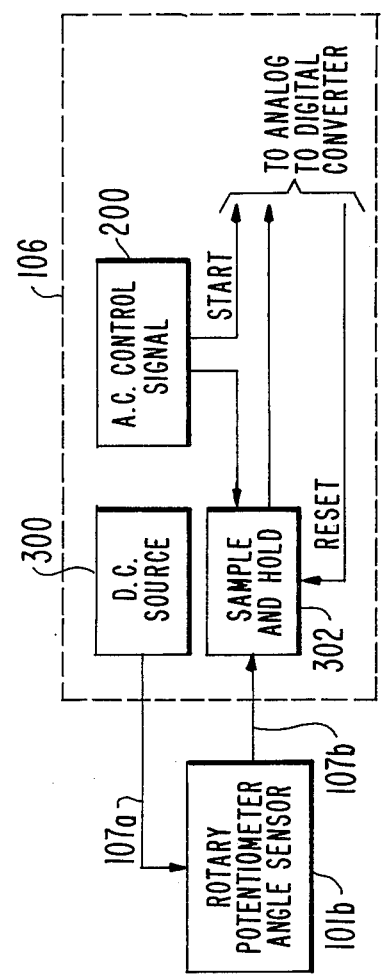

In the drawings:

FIG. 1 is a block diagram of a pulse-echo ultrasonic wave energy imaging system incorporating the present invention;

FIG. 1a schematically illustrates the linkage between the mechanically-oscillated transducer and the mechanical portion of the scanning means of FIG. 1;

FIG. 2 is a block diagram of an embodiment of the analog angle sensor and electronic portion of the scanning means of FIG. 1, and FIG. 3 illustrates a modification of the embodiment shown in FIG. 2.

Referring to FIG. 1, mechanically-oscillated electro-acoustic transducer 100 and angle sensor 101 are completely immersed in ultrasonic wave propagating liquid 102, which may be water. As indicated by dashed line 104, transducer 100 and angle sensor 101 are mechanically linked to scanning means 106. Scanning means 106 includes a mechanical portion, which together with linkage 104 transducer 100 and angle sensor 101, are shown in detail in FIG. 1a discussed below. Scanning means 106 further includes an electronic portion, embodiments of which are shown in FIGS. 2 and 3, which electronic portion is electrically coupled to angle sensor 101 over connection 107. Further, the electronic portion of scanning means 106 derives a trigger and a scan position signal. The scan position signal normally controls the horizontal deflection circuit of B-scan display 108 in accordance with the then-existing angular position of the oscillated transducer (while range controls the vertical deflection). In addition, the trigger pulse output from scanning means 106 is applied as an input to ultrasonic frequency (UF) pulse source 110, which energizes transducer 100 with a UF pulse (i.e., a frequency in the range of 1.0–10 MHz) in response to each trigger applied thereto. This results in a pulsed beam of ultrasonic wave energy being generated by transducer 100. The ultrasonic wave energy is propagated through a liquid 102 to insonify structure 112. Structure 112 (which may be a portion of a human body) returns ultrasonic wave energy echoes to transducer 100, where they are detected as electrical signals. The detected signals are applied through imaging electronics 114 to an intensity modulating electrode of B-scan display 108.

As shown in FIG. 1a, the mechanical portion of scanning means 106 comprises a revolving member consisting of shaft 120 and a supporting wheel 122. This revolving member is revolved at a uniform angular velocity by drive 124. Linkage 104 comprises rod 126 having one end thereof coupled to point 128 located near the periphery of wheel 122. Transducer 100 is rotatably mounted with respect to the axis of support member 130 thereof. The other end of rod 126 is coupled to one end of transducer 100 through universal joint 132. Angle sensor 101, which is energized from the electronic portion of scanning means 106 over conductor 107a, includes a rotatable member attached to support member 130 that rotatably moves as a unit with transducer 100 about the axis of support member 130. An output signal, that is an analog of the then-existing angular position of oscillated transducer 100, is forwarded to the electronic portion of scanning means 106 over conductor 107b.

During each revolution of the revolving member, the angular position $\phi$ of shaft 120, wheel 122 and, hence, point 128 varies linearly between 0° and 360°. Movement of point 128 imparts oscillating movement to transducer 100 and the rotatable member of angle sensor 101 through linkage 104. Specifically, during each revolution of point 128, transducer 100 and the rotatable member of angle sensor 101 are angularly rotated about axis 130 through one complete cycle of oscillation. During each cycle of oscillation, the angular position $\theta$ of transducer 100 and the rotatable member of angle sensor 101, vary from a first angular limit $\theta_1$ through 0 to a second angular limit $-\theta_1$; and back again through 0 to the first angular limit $\theta_1$.

The rate of oscillation of transducer 100 and angle sensor 101 is high (e.g. in the range of 100–1500 cycles per minute). For illustrative purposes in describing the invention, it is assumed that the rate of oscillation is about 300 cycles per minute, (i.e., 5 cycles per second).

During the period of each cycle of oscillation, the angular velocity of transducer 100 and the rotatable member of angle sensor 101, which vary sinusoidally, reaches a maximum whenever $\theta=0$ and becomes zero whenever $\theta$ equals $\theta_1$ or $-\theta_1$. During each cycle of oscillation, transducer 100 serially transmits a predetermined number of successive UF pulses. However, since the angular velocity of transducer 100 is not linear, but sinusoidal, in order to achieve uniform sampling of the insonified structure, the total angular displacement $2\theta$ of transducer 100 during each complete cycle of oscillation is divided into a corresponding predetermined number of equal increments in angular position of transducer 100, at which each successive UF pulse is transmitted during each cycle of oscillation. For illustrative purposes, it is assumed that the predetermined number of equal angular increments (and, hence, predetermined number of successive UF pulses) during each cycle of oscillation is 200.

Referring to FIG. 2, the angle sensor preferably takes the form of a rotary variable differential transformer angle sensor 101a. As is known, such a transformer includes a secondary coil having two differential secondary windings which are magnetically coupled to a primary coil by a rotatable magnetically permeable slug. The primary coil is energized with a relatively high frequency (e.g. 5 KHz) AC control signal from block 200 over conductor 107a. The rotatable slug of sensor 101a is preferably oriented so that, in the secondary winding, a small signal is induced at one extreme angular position (e.g., $-\theta_1$), a larger signal is induced in the zero angular position and the largest signal is induced at the other extreme angular position (e.g., $+\theta_1$) of oscillated transducer 100 (see FIG. 1a). So long as the maximum angular displacement from $-\theta_1$ to $+\theta_1$ of oscillated transducer 100 is relatively small (e.g., in order of 30° or less), the output signal from the differential secondary windings has an amplitude substantially proportional to its angular displacement. A benefit of using a rotary variable differential transformer as the angle sensor is that it can be completely immersed in the propagating medium without requiring a sealed unit.

The output signal derived across the two differential secondary windings of angle sensor 101a is applied over conductor 107b as an input to demodulator, peak and hold means 202. Means 202, in response to a reset signal applied thereto, derives an output signal therefrom having an analog value which is proporational to the demodulated peak amplitude of the input signal to means 202 from sensor 101a at that time. This output signal from means 202 (which is held until the next reset signal is applied to means 202) is applied as an analog sample input of the angular position of transducer 100 to analog-to-digital converter 204. At a certain point in each cycle of the AC control signal from block 200, a start signal is applied to analog-to-digital converter 204. Converter 204, by comparing the value of the input thereto from means 202 with that of a reference voltage $V_{REF}$, derived from potentiometer 206, produces an n-bit digital output signal representing the analog value of the input signal to converter 204. More specifically, potentiometer 206 is adjusted to provide a value of $V_{REF}$ such that the least significant bit of the n-bit digital output of converter 204 corresponds with a predetermined-size angular increment of transducer 100. For instance, assuming each cycle of oscillation is divided into 200 equal angular increments, converter 204 provides at least an 8-bit digital output (i.e. has a capacity of at least 256) to accommodate each of the 200 equal angular increments in angular position into which each cycle of oscillation is divided. However, because the angular velocity of oscillation is sinusoidal, rather than linear, the time interval required for the angular position of the transducer to change by one angular increment varies during a cycle of oscillation. Assuming transducer 100 oscillates at 300 cycles per minute (5 cycles per second) and each cycle is divided into 200 equal increments in angular position, the shortest time interval required to traverse a single increment in angular position is no less than 1/3200 seconds. Since the assumed sampling rate is 5 KHz, each of the 200 increments in angular position of cycle of oscillation is necessarily sampled at least one time during each complete cycle.

At the end of each sampling period, converter 204 applies a reset signal to demodulator, peak and hold means 202 and an enable signal to digital comparator 208. In response to this reset signal, means 202 dumps the old sample being held and replaces it with a new sample of the then-present demodulated peak value of the analog signal input to means 202 from angle sensor 101a. In response to the enable signal, digital comparator 208 compares the digital value of the n-bit output of converter 204 with the digital value of the n-bit output of first n-bit latch 210. If both these two digital values are the same, nothing happens. However, if the digital value of the n-bit output from converter 204 is greater than that from latch 210, comparator 208 produces a plus (+) output signal. If the digital value of the n-bit output from converter 204 is less than that of latch 210, comparator 208 produces a minus (−) output signal. Both the plus and minus output signals from comparator 208 are applied through OR gate 214 as an input to a one-shot pulse generator 216 and as a load input signal to first latch 210. In response to this load input signal, latch 210 is loaded with the then-existing digital value of the n-bit output from converter 204.

As indicated in FIG. 1a, the angular displacement between $-\theta_1$ and $\theta_1$ of transducer 100 during a first half of each cycle of oscillation and during the second half of each cycle of oscillation covers the same total angular interval. The only difference is that the angular position of transducer 100 is increasing during that half-cycle when it is traveling in a positive direction from $-\theta_1$ to $\theta_1$ and is decreasing during that half-cycle when it is traveling in a negative direction from $\theta_1$ and $-\theta_1$. It is desirable that the scanning of the insonified structure be interlaced. This is accomplished by scanning odd lines during one of the two half-cycles of oscillation and scanning even lines during the other of the two half-cycles of oscillation.

Since flip-flop 212 is set by a plus (+) output from digital comparator 208, flip-flop 212 in its set state is indicative of transducer 100 being angularly displaced in a positive direction from $-\theta_1$ to $\theta_1$. Similarly, since flip-flop 212 is reset by a minus (−) output from digital comparator 208, flip-flop 212 in its reset state is indicative of transducer 100 being angularly displaced in a negative direction from $\theta_1$ to $-\theta_1$.

The least significant bit of the digital value of the n-bit output of latch 210 is applied as a first input to exclusive OR gate 218 and the Q output from flip-flop 212 (indicative of which state flip-flop 212 is then in) is applied as a second input to exclusive OR gate 218. The output from exclusive OR gate 218 is used to open normally-closed (disabled) gate 220.

The output from one-shot pulse generator 216 forwarded through normally-closed gate 220 constitutes the trigger output from the electronic portion of scanning means 106. In addition, the output from one-shot pulse generator 216 forwarded through normally-closed gate 220 is used as a load signal for second n-bit latch 222. In response to a load signal applied to second n-bit latch 222, the digital value of the n-bit output from first latch 210 is transferred to second latch 222. The digital value of the n-bit output of second latch 222, after being converted to analog form by digital-to-analog converter 224, constitutes the scan-position signal output of the electronic portion of scanning means 106.

As shown in FIG. 3, rotary potentiometer angle sensor 101b (which must be sealed when immersed in the propagating liquid) may be substituted for rotary variable differential transformer angle sensor 101a. In this case, the rotary potentiometer is energized from DC source 300, rather than from AC control signal source 200. In addition, sample and hold means 302 replaces demodulator, peak and hold means 202. The sampling rate of sample and hold means 302 is determined by an output from AC control signal source 200 (which is still assumed to at a frequency of 5 KHz). In all other respects, the embodiment shown in FIG. 3 is similar to that shown in FIG. 2.

What is claimed is:

1. In a pulse-echo ultrasonic wave energy imaging system comprising (1) a mechanically-oscillated electro-acoustic transducer responsive to the energization thereof for generating a scanning beam of pulsed ultrasonic wave energy that is propagated through a given liquid toward a remotely-located given structure to be insonified, said structure returning ultrasonic wave energy echoes propagated through said liquid to said transducer for detection and display on a display device of an image of said insonified structure, wherein said transducer is completely immersed in said liquid and is mounted for angular movement about a given axis; (2) an angle sensor for deriving an output signal which is a predetermined function of the angular position of said mechanically-oscillated transducer, and (3) electronic means responsive to said output signal from said angle sensor for energizing said transducer at each of a group of specified angular positions of said transducer during each cycle of oscillation thereof; the improvement therein:

wherein said angle sensor comprises an analog angle sensor immersed in said propagation liquid and directly coupled to said transducer for deriving a continuous output signal having a value which is substantially proportional to the then-existing angular position of said oscillated transducer, and wherein said electronic means comprises an analog-to-digital converter for producing a multi-bit digital output of the angular position of said oscillated transducer in which the least significant bit corresponds with a predetermined angular incremental change in the angular position of said oscillated transducer, first means for periodically applying a sample of said analog sensor output signal to the input of said analog-to-digital converter at a rate sufficiently high that said analog angle sensor output signal is sampled at least once during each successive angular incremental change of said oscillated transducer, and second means operative during the occurrence of a certain one of the two half-cycles of each oscillation of said transducer for energizing said transducer in response to the occurrence of each successive odd value of the least significant bit of the digital output of said analog-to-digital converter and operative during the occurrence of the other one of the two half-cycles of each oscillation of said transducer for energizing said transducer in response to the occurrence of each successive even value of the least significant bit of the digital output of said analog-to-digital converter.

2. The system defined in claim 1, wherein said analog angle sensor comprises a rotary variable differential transformer.

3. The system defined in claim 1, wherein said analog angle sensor comprises a rotary potentiometer.

4. The system defined in claim 1, wherein said second means includes a digital latch responsive to a load signal applied thereto for storing the then-existing multi-bit digital output of said analog-to-digital converter, a digital comparator operative at the end of the application of each successive sample for comparing the digital value of the output of said analog-to-digital converter with that stored in said latch to produce a first output from said comparator only when the digital value of the output of said analog-to-digital converter is greater than that stored in said latch and produce a second output from said comparator only when the digital value of the output of said analog-to-digital converter is less than that stored in said latch, a flip-flop set by a first output from said comparator and reset by a second output from said comparator, a one-shot pulse generator and a normally closed gate for triggering the energization of said transducer in response to a generated pulse being forwarded through said gate, an exclusive OR gate for opening said normally closed gate when said flip-flop has a certain one of its two states and the least significant bit stored in said latch is odd or when said flip-flop has the other of its two states and the lowest significant bit stored in said latch is even, and an OR gate for applying a load signal to said latch and for operating said pulse generator in response to either a first or a second output from said comparator.

5. The system defined in claim 4, wherein said electronic means includes a second digital latch responsive to a load signal applied thereto for transferring the digital value then being stored in said first-mentioned latch to said second latch for storage therein; and means for applying each generated pulse forwarded through said normally closed gate as a load signal to said second latch, and a digital-to-analog converter responsive to the digital value stored in said second latch for driving a scan position signal for said display device.

* * * * *